United States Patent
Pagan

(10) Patent No.: US 6,378,522 B1
(45) Date of Patent: Apr. 30, 2002

(54) RESPIRATION ASSEMBLIES AND INDICATORS

(75) Inventor: Eric Pagan, Hythe (GB)

(73) Assignee: Smiths Industries Public Limited (GB)

( * ) Notice: Subject to any disclaimer, the term of this patent is extended or adjusted under 35 U.S.C. 154(b) by 0 days.

(21) Appl. No.: 09/386,227

(22) Filed: Aug. 31, 1999

(30) Foreign Application Priority Data

Sep. 2, 1998 (GB) .............................................. 9819089

(51) Int. Cl.⁷ .............................................. A61M 16/00
(52) U.S. Cl. .......................... 128/207.14; 128/205.23; 128/202.22; 128/202.27
(58) Field of Search ....................... 128/207.14, 205.23, 128/202.22, 205.28, 202.27, 200.26, 205.13

(56) References Cited

U.S. PATENT DOCUMENTS

| | | | |
|---|---|---|---|
| 4,691,701 A | | 9/1987 | Williams |
| 4,790,327 A | * | 12/1988 | Despotis ..................... 128/719 |
| 4,821,710 A | | 4/1989 | Greunwald et al. |
| 4,852,564 A | * | 8/1989 | Sheridan et al. ........ 128/202.27 |
| 4,919,127 A | * | 4/1990 | Pell ........................ 128/207.14 |
| 4,994,117 A | * | 2/1991 | Fehder ................... 128/207.14 |
| 5,005,572 A | * | 4/1991 | Raemer et al. ......... 128/207.14 |
| 5,291,879 A | * | 3/1994 | Babb et al. ............. 128/200.26 |
| 5,367,292 A | | 11/1994 | Szoke et al. |
| 5,375,592 A | | 12/1994 | Kirk et al. |
| 5,421,325 A | * | 6/1995 | Cinberg et al. ......... 128/200.26 |
| 5,456,249 A | * | 10/1995 | Kirk ....................... 128/205.13 |
| 5,517,985 A | | 5/1996 | Kirk et al. |
| 5,749,358 A | * | 5/1998 | Good et al. ............. 128/205.23 |

FOREIGN PATENT DOCUMENTS

| | | |
|---|---|---|
| GB | 2 264 869 | 9/1993 |
| WO | WO 89/07956 | 8/1989 |
| WO | WO 89/07957 | 8/1989 |
| WO | WO 90/01695 | 2/1990 |
| WO | WO 97/14464 | 4/1997 |

* cited by examiner

Primary Examiner—John G. Weiss
Assistant Examiner—V. Srivastava
(74) Attorney, Agent, or Firm—Connolly Bove Lodge Hutz LLP

(57) ABSTRACT

An indicator for detecting correct intubation of an endotracheal tube has a paper color-change element attached to a frame that is removably secured in a transparent connector in the machine end of the tube. A handle on the frame extends along the outside of the connector so that the indicator can be removed from the machine end of the connector by pulling the handle. The indicator prevents another connector being attached to the connector in the tube until after the indicator has been removed.

4 Claims, 2 Drawing Sheets

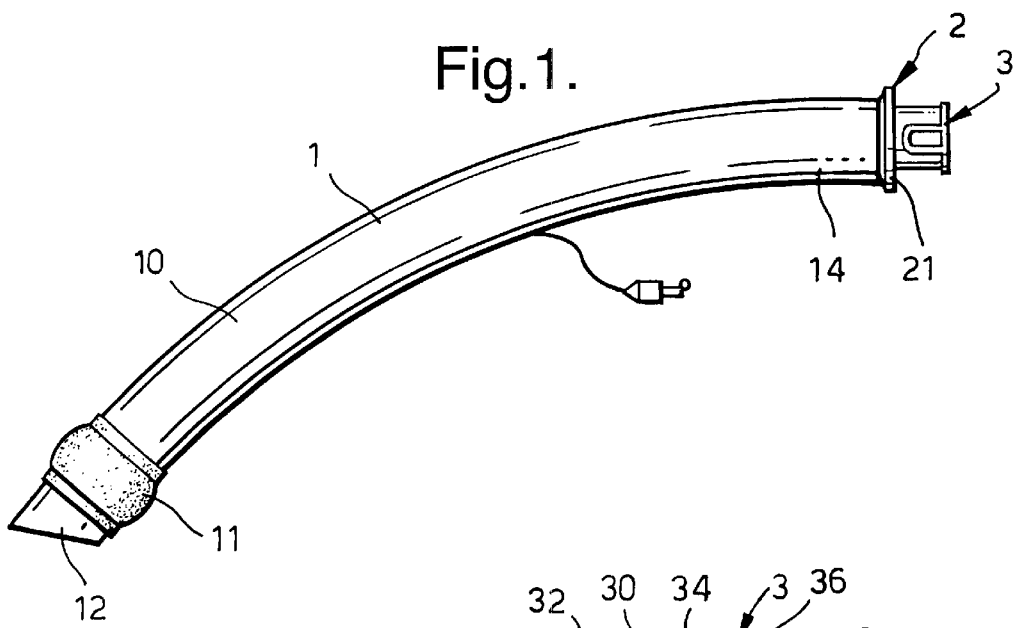
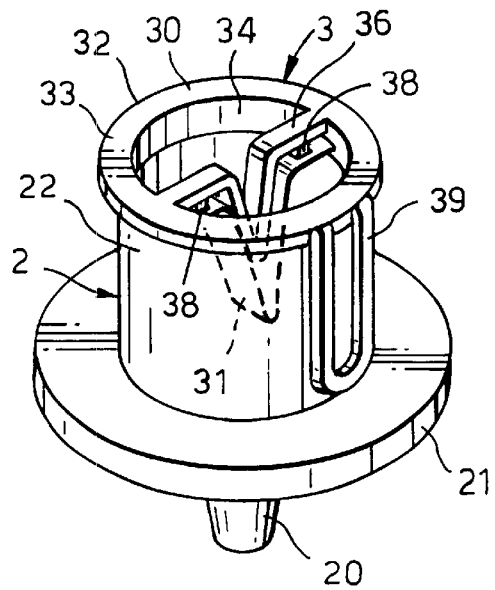
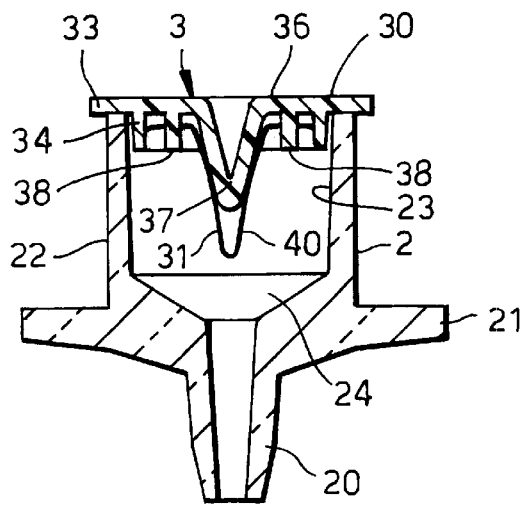

RESPIRATION ASSEMBLIES AND INDICATORS

BACKGROUND OF THE INVENTION

This invention relates to respiration assemblies and to indicators.

The invention is more particularly concerned with assemblies with provision for detecting correct placement of an endotracheal tube or for indicating patient breathing.

One of the major problems associated with the use of an endotracheal tube is that of ensuring that the patient end of the tube is correctly located in the trachea and not in the esophagus. There are various ways in which correct intubation can be detected. The usual way is to connect the machine end of the tube to a capnograph, which is responsive to the levels of carbon dioxide. When the tube is correctly inserted, the level of carbon dioxide detected will rise and fall with the patient's breathing. By detecting this alternating level of carbon dioxide, correct intubation is indicated. If the tube is incorrectly inserted, in the oesophagus, any carbon dioxide produced by the digestive system will be at a relatively steady level. Capnographs can produce a reliable indication of correct intubation but the equipment is relatively bulky and expensive so it is only available in well-equipped surgical operating theatres.

An alternative device can be used to detect carbon dioxide, which includes a chemical color-change indicator, such as described in, for example, WO96/24054, EP509998, U.S. Pat. Nos. 5005572, 4879999, EP257916, U.S. Pat. Nos. 4691701, 4790327, WO89/07956, GB2218515 and U.S. Pat. No. 4728499. This form of device usually comprises a paper or some other substrate that is impregnated or coated with the chemical including a pH-sensitive indicator dye, the substrate preferably being provided in some form of transparent connector attached to the machine end of the tube. Such indicators can be of low cost and can provide a clear indication that the tube has been correctly inserted. If the indicator fails to change color, the clinician knows immediately that the tube has been incorrectly inserted. These prior indicators are designed to be left in position on the connector during use of the tube. This can, however, be a disadvantage because, to be effective, the indicator must be exposed to the maximum gas flow, thereby inevitably providing some impediment to gas flow. Also, where the indicator is positioned in the main gas flow path, this may prevent access to the tube, such as by a suction catheter or the like.

It is also useful in some circumstances to have a readily visible indicator confirming that the patient is breathing on other respiration devices, such as face masks or the like.

BRIEF SUMMARY OF THE INVENTION

It is an object of the present invention to provide an improved respiration assembly and indicator.

According to one aspect of the present invention there is provided a respiration assembly including a respiration device, a housing mounted with the respiration device and an indicator assembly mounted in the housing, the indicator assembly having an indicator element mounted to extend within a lumen through the housing, and the indicator assembly being detachably secured in the housing such that the indicator assembly can be removed from the machine end of the housing.

The housing is preferably of a transparent plastics material and is preferably a connector. The indicator assembly is preferably shaped to prevent the connector mating with another connector while the indicator assembly is secured with the connector. The indicator assembly may be a push fit in the machine end of the housing. The indicator assembly preferably comprises a frame and an indicator element supported on the frame. The frame may comprise a circular ring attached coaxially with one end of the housing and a projecting member extending substantially axially of the housing, the indicator element being supported on the projecting member. The indicator element is preferably of a paper including a carbon-dioxide color-change indicator chemical. The indicator assembly preferably includes a handle extending along the outside of the housing by which the indicator assembly can be gripped to remove it from the housing. The respiration device may be an endotracheal tube.

According to another aspect of the present invention there is provided an indicator for indicating patient breathing, the indicator having an outer housing adapted for connection at one end to a respiration device and an indicator assembly detachably secured in the housing and removable from the opposite end of the housing.

According to a further aspect of the present invention there is provided a method of determining correct intubation of a patient comprising the steps of introducing into the trachea of the patient an endotracheal tube assembly of the kind including an endotracheal tube, a connector mounted at the patient end of the tube and an indicator assembly mounted in the connector, observing the indicator assembly to ensure correct intubation, and subsequently removing the indicator assembly from the connector while leaving the connector in position on the tube.

An endotracheal tube assembly and its method of use, in accordance with the present invention, will now be described, by way of example.

BRIEF DESCRIPTION OF THE DRAWINGS

FIG. 1 is a side elevation view of the assembly;

FIG. 2 is a perspective view of a part of the assembly to a larger scale;

FIG. 3 is a sectional side elevation view of the part shown in FIG. 2;

DETAILED DESCRIPTION OF THE PREFERRED EMBODIMENTS

Figure 4:
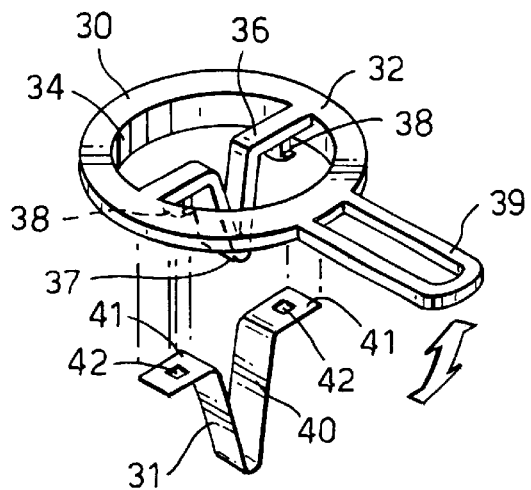
FIG. 4 is an exploded, perspective view of the part shown in FIGS. 2 and 3.

With reference first to FIG. 1, the assembly comprises an endotracheal tube 1, a connector 2 mounted in the machine end of the tube, and an indicator assembly 3 mounted in the connector.

The endotracheal tube 1 is of conventional construction, comprising a curved tubular shaft 10 with an inflatable cuff 11 encircling the shaft close to the open, patient end 12. The machine end 14 of the tube I is also open and is securely connected to the connector 2, which is shown in more detail in FIGS. 2 to 4, and takes the form of a breathing indicator.

The connector 2 is moulded from a rigid, transparent plastics material and has a tapered forward end 20 of relatively small diameter, which is a push fit within the machine end 14 of the tube 1 and may be bonded to it by means of a solvent or adhesive. Midway along its length, the connector has a radially-projecting flange 21, which divides the forward end 20 from the rear or machine end 22. The rear end 22 is enlarged with an external diameter of 15mm and a shallow luer taper adapted to receive a cooperating female tapered connector. The interior of the forward and rear ends 20 and 22 communicate with one another, forming a bore or lumen 24 through the connector.

The indicator assembly 3 comprises a moulded plastic support frame 30 and an indicator element 31 retained on the frame. The frame 30 has an outer, circular ring 32, which, in section is of angled shape, having a horizontal portion 33, which sits coaxially on the end of the rear end 22 of the connector 2 providing a housing for the assembly 3. The frame 30 has a vertical portion 34, which is a tight fit within the rear end of the connector and may have barbs or fins to improve the grip on the inside of the connector 2. The frame 30 also has a lateral bar 36 extending diametrically across the ring 32, the central part of the bar being bent down or forwardly into a V-shape formation 37, projecting axially of the connector 2. The underside of the bar 36 has two fixing lugs 38 with arrow-shape heads projecting down on opposite sides of the V-shape formation 37. The frame 30 also has a lever 39 of rectangular shape attached with the outside of the ring 32 by two reduced thickness hinge portions 40. The lever 39 normally extends down or forwardly along the outside of the rear part 22 of the connector 2.

The indicator assembly 3 is completed by the indicator element 31. The indicator element 31 is a strip of paper into which is absorbed a conventional carbon dioxide color-change indicator chemical, which may be of the kind described in any of the patents referred to in the introduction. The indicator strip 31 is bent to form a central V-shape portion 40 conforming to the shape of the V-shape formation 37 on the frame 30. The ends 41 of the strip 31 extend horizontally outwardly and have fixing holes 42 shaped and positioned to receive the heads of the fixing lugs 38. The strip 31 is mounted underneath the lateral bar 36, with the V-shape portion 40 extending around the V-shape formation 37 on the bar 36 and with the ends 41 being retained by the fixing lugs 38. The indicator strip 31 extends across the lumen 24 of the connector 2, with the lower, central portion 40 projecting down within the connector along a major part of the length of its rear end 22. The dimensions of the indicator assembly 3 and the indicator strip 31 are such that the strip is clearly visible through the wall of the connector 2, whilst allowing air to flow along the lumen 24 of the connector.

The indicator assembly 3 is removable from the rear end of the connector 2, as shown in FIG. 4, by gripping the lower end of the lever 39, lifting this up so that it hinges about the hinge portions 40, and then pulling the indicator by the lever rearwardly out of the connector.

Figure 5:
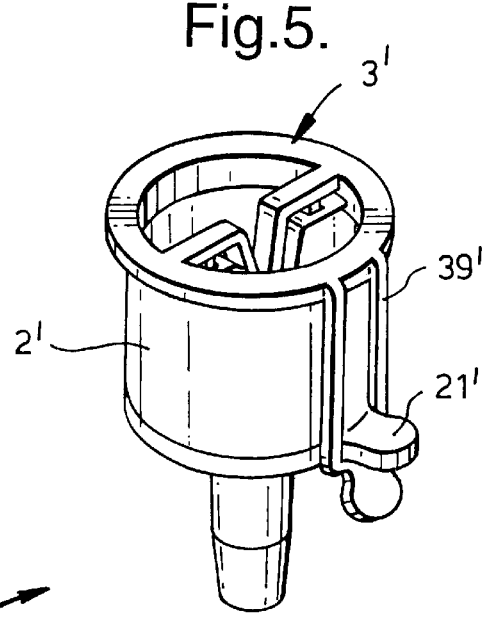
FIG. 5 is a perspective view of an alternative part of the assembly.

There are various other ways in which a similar indicator assembly could be attached to a connector instead of by the push, friction fit described above. For example, the indicator assembly and connector could be threaded so that the indicator assembly is removed by unscrewing. Alternatively, the indicator assembly and connector could have cooperating surface formations that snap fit together. In other arrangements, the indicator assembly could be attached with the connector by a tear seal, or by a spot or tack weld. A further arrangement is shown in FIG. 5 where the indicator assembly 3' has a hinged or flexible clip 39' that fastens over a lug 21' projecting outwardly of the connector 2'.

Figure 6:
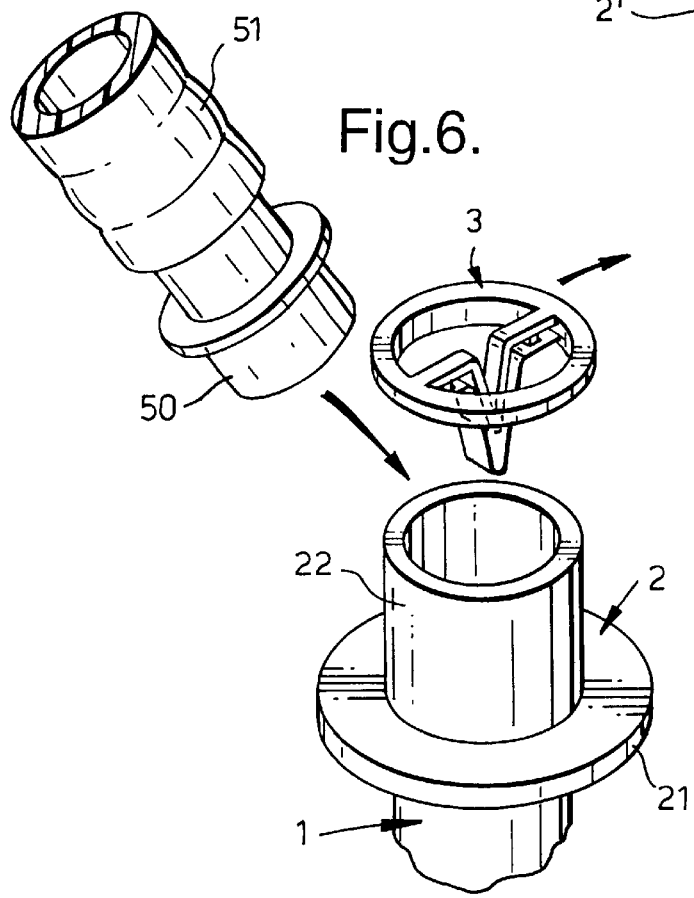
FIG. 6 illustrates steps in the use of the assembly.

In use, the assembly is supplied with the connector 2 and indicator assembly 3 ready fitted in the machine end 14 of the tube 1, so that the clinician can readily insert the tube into the patient without the need for further assembly. If the tube 1 is correctly inserted with its patient end 12 located in the trachea, the indicator assembly 3 will be exposed to the patient's inhaled and exhaled breath flowing along the tube. Because the exhaled breath contains a relatively high concentration of carbon dioxide, this causes the indicator strip 31 to change color during exhalation. When the patient inhales, the color of the strip 31 changes back towards its normal color. In this way, the color of the indicator strip 31 alternates with the patient's breathing. The clinician observes the indicator assembly 3 and, when this confirms correct intubation, he inflates the cuff 11 to seal the tube 1 with the trachea and to retain it in position. He then removes the indicator assembly 3 by pulling it out of the connector 2 in the way described above, and as shown in FIG. 6, so as to maximize the passage through the connector and enable access by a suction catheter or the like should this be necessary. If the patient is breathing spontaneously, the connector 2 may be left open. If assisted ventilation is needed, the connector 2 can be connected to a cooperating male connector 50 connected to ventilation tubing 51 extending to ventilation equipment (not shown). If the indicator assembly 3 were left in place, it would prevent connection by the ventilation connector 50; this ensures that the indicator assembly is removed before connection.

The invention could be used with other respiration devices than endotracheal tubes. For example, an indicator according to the invention could be provided on a face mask to indicate patient breathing.

What I claim is:

1. An endotracheal tube assembly comprising: an endotracheal tube having a patient end and a machine end; a transparent connector having a patient end and a machine end, said patient end of said connector being secured in said machine end of said endotracheal tube; and an indicator assembly mounted in said connector, wherein said indicator assembly includes a frame and an indicator element mounted on the frame to extend within a lumen through said connector, wherein said frame includes a ring member and a bar member extending laterally of the ring member and having a portion thereof extending axially of the connector, wherein said frame is detachably secured in said connector wherein said indicator element is a strip of material attached with said bar member, said strip of material including a carbon dioxide color-change indicator chemical and wherein said indicator assembly is manually accessible externally of said connector such that said indicator assembly can be removed from the said machine end of said connector.

2. An assembly according to claim 1 wherein said indicator assembly has a part projecting over a mating surface of said connector to prevent said connector mating with another connector while said indicator assembly is secured with said connector.

3. An assembly according to claim 1, wherein said indicator assembly is a push fit in the said machine end of said connector.

4. An assembly according to claim 1, wherein said indicator assembly includes a handle extending along an outside of said connector by which said indicator assembly can be gripped to remove it from said connector.

* * * * *